(12) United States Patent
Capparella et al.

(10) Patent No.: US 7,544,843 B2
(45) Date of Patent: Jun. 9, 2009

(54) PROCESS FOR PREPARING 3,4-DIOXO-SUBSTITUTED AROMATIC ALDEHYDES

(75) Inventors: Elisa Capparella, Ravenna (IT); Elisa Poluzzi, Calederara Di Reno (IT); Valerio Borzatta, Bologna (IT)

(73) Assignee: Endura S.p.A., Bologna (IT)

( * ) Notice: Subject to any disclaimer, the term of this patent is extended or adjusted under 35 U.S.C. 154(b) by 0 days.

(21) Appl. No.: 11/996,723

(22) PCT Filed: Jul. 25, 2006

(86) PCT No.: PCT/EP2006/064622

§ 371 (c)(1),
(2), (4) Date: Jul. 8, 2008

(87) PCT Pub. No.: WO2007/012641

PCT Pub. Date: Feb. 1, 2007

(65) Prior Publication Data

US 2009/0062569 A1     Mar. 5, 2009

(30) Foreign Application Priority Data

Jul. 25, 2005   (IT) ................ MI2005A1431

(51) Int. Cl.
C07C 45/29   (2006.01)
(52) U.S. Cl. .................................. 568/426
(58) Field of Classification Search ......... 568/326
See application file for complete search history.

(56) References Cited

U.S. PATENT DOCUMENTS 4,663,488 A * 5/1987 Locko et al. ............. 568/485
6,703,527 B2 * 3/2004 Tanikawa et al. ........ 568/315

OTHER PUBLICATIONS

Creyghton, et al. (1997) "Stereoselective Meerwein-Ponndort-Verley and Oppenauer Reactions Catalysed by Zeolite BEA"; *Journal of Molecular Catalysis A: Chemical*; 115:457-472.
Djerassi, C. (1951) "The Oppenauer Oxidation"; *Organic Reactions*; vol. VI; Chapter 5; 207-272.
Graauw et al. (1994) "Meerwein-Ponndort-Verley Reductions and Oppenauer Oxidations: An Integrated Approach; Synthesis";1007-1017.
Grigor'ev, et al. (1989) "Use of 1-Hydroxybenzotriazole-Based Polymeric Activated Esters in Peptide Synthesis"; *Zhurnal Organicheskoi khimii*; 25:1963-1967.
Hon, et al. (2004) "Tishchenko reactions and Oppenauer oxidation reactions of aldehydes promoted by diisobutylaluminum hydride": *Tetrahedron Letters*: 45:3313-3315.
International Preliminary Report on Patentability for PCT/EP2006/064622.
Lin, et al. (1952) "A Study of the Mixed Tischtschenko Reaction": *Contribution from the Department of Chemistry of the University of Pennsylvania*: 5133-5135.
March, J. (1977) "Aromatic Electrophilic Substitution": *Advanced Organic Chemistry*; 419-420; McGraw-Hill; Texas, US.
Marie-Robert De Maheas, M.R. (1989-1999) "La Réation de A. Vilsmeier et A. Haack"; *Mise Au Point*; Article in French.

* cited by examiner

*Primary Examiner*—Sikarl A Witherspoon
(74) *Attorney, Agent, or Firm*—Knobbe Martens Olson & Bear LLP

(57) ABSTRACT

A new process for synthesizing 3,4-dioxo-substituted aromatic aldehydes by Oppenauer oxidation of the corresponding benzyl alcohols is described. The process, which specifically uses formaldehyde as hydrogen acceptor, proceeds with unexpectedly high yields and conversion percentages, allowing low cost access to finished and intermediate products of high industrial interest in the field of pharmaceutical products and fragrances.

15 Claims, No Drawings

PROCESS FOR PREPARING 3,4-DIOXO-SUBSTITUTED AROMATIC ALDEHYDES

RELATED APPLICATIONS

This application is a U.S. National Phase of International Application No. PCT/EP2006/064622, filed Jul. 25, 2006, designating the U.S. and published in English as WO 2007/012641 on Feb. 1, 2007, which claims the benefit of Italian Application No. MI2005A001431.

FIELD OF THE INVENTION

The present invention relates to the synthesis of aromatic aldehydes obtained from the corresponding benzyl alcohols by oxidation reaction with formaldehyde.

PRIOR ART

Aromatic aldehydes are products of broad commercial interest, used both as finished products and as intermediates in the preparation of further compounds.

Finished products include for example 3,4-methylenedioxybenzaldehyde (known as heliotropin or piperonal), used in the fragrance industry. Intermediates include the above cited product, as an intermediate in the production of perfumes such as helional, and 3,4-dimethoxybenzaldehyde (veratraldehyde), as an intermediate in the synthesis of the known vasodilator Verapamil.

Several methods are reported for the synthesis of aromatic aldehydes.

For example aromatic aldehydes can be obtained by the Reimer-Tiemann reaction (March, *Advanced Organic Chemistry*, 419-420, McGraw-Hill) from the appropriate aromatic compound with chloroform in sodium hydroxide. However, this method presents the disadvantage of using a highly toxic chlorinated reagent/solvent, classed as carcinogenic.

Another reaction used is the Vilsmeier-Haack, by reacting the appropriate aromatic compound with phosphorus oxychloride and disubstituted formamides (de Maheas, *Bull.Soc..Chim.France,* 1962, 1989-1999) or with N-substituted formanilides (GB 1591268). However, the reaction has the disadvantage of a particularly costly treatment of the processing waters and precipitation of phosphorus salts.

Aromatic aldehydes can also be obtained by oxidizing the corresponding benzyl alcohols with air or oxygen in the presence of catalysts consisting of noble metals, such as Pd, Pt, Ru in the presence of salts of heavy metals such as salts of lead, bismuth, silver or tin (JP 55022615 and JP 57009734). In this case also the catalyst must be recycled, and special treatments are needed for disposing of the aforesaid heavy metals.

The Oppenauer reaction has been used for aromatic aldehyde synthesis by reacting the corresponding benzyl alcohols with aliphatic ketones and aliphatic or aromatic higher aldehydes as hydrogen acceptors, in the presence of aluminium alkoxides or aryloxides (Djerassi, *Organic Reactions*, vol.VI, chapter. 5, Wiley and Sons; De Graauw, C. F. et al., *Synthesis,* 1007-1017, 1994) or in the presence of heterogeneous catalysts, such as BEA zeolite (Creyghton, E. J., et al., *Journal of Molecular Catalysis A: Chemical* 115(1997), 457-472).

However, this reaction presents a number of drawbacks, including, especially when an aldehyde is used as hydrogen acceptor, formation of esters caused by the Tishchenko reaction (Day, A. R, JACS 1952, 74, 5133; Hon, Y. S., *Tetrahedron Letters* 2004, 45(16), 3313-3315). Moreover, the presence of aldehyde and ketone species, with alpha hydrogens on the carbonyl group, gives rise, under reaction conditions, to aldol condensations with formation of a number of by-products that influence the final reaction yield.

The Oppenauer reaction has also been used for the oxidation of aliphatic alcohols, particularly allyl alcohols, as reported in U.S. Pat. No. 4,663,488 or in U.S. Pat. No. 6,703,527.

Attempts at oxidation with formaldehyde are rare and poorly effective. Patent application FR 2 835 251 demonstrates the preparation of monosubstituted aromatic aldehydes by oxidation of the corresponding benzyl alcohol in the presence of formaldehyde; the reaction proceeds with modest yields, and requires the use of expensive catalysts doped with metals.

*Zhurnal Organicheskoi Khimii* (1989), 25(9), 1963-7 describes the synthesis of 3-nitro-4-chlorobenzaldehyde by oxidation of the corresponding alcohol with formaldehyde in aqueous solution and sodium hydroxide; the reaction is conducted in methanol with a 50% yield.

SUMMARY

We have now found that, by reacting 3,4-dioxo-substituted benzyl alcohols with formaldehyde in the presence of common oxidation catalysts, the Oppenauer reaction proceeds with an unexpectedly high efficiency to obtain nearly quantitative yields and conversion percentages. The invention specifically relates to the oxidation of benzyl alcohols of formula (II)

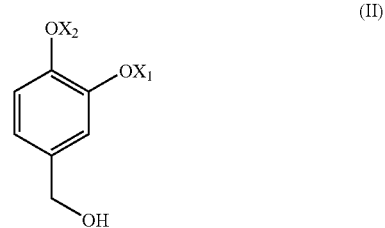

where $X_1$ and $X_2$, the same or different from one another, represent hydrogen, linear or branched C1-C8 alkyl, with the proviso that at least one of $X_1$ and $X_2$ is different from hydrogen, or $(OX_1)$ and $(OX_2)$, taken together, form a —O-T-O— group where T is a C1-C3 alkylene optionally substituted with C1-C5 alkyl, to obtain the corresponding aromatic aldehydes of formula (I)

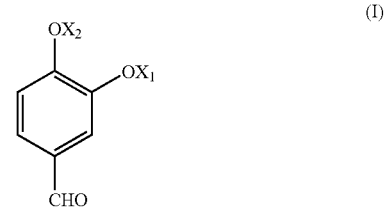

where $X_1$ and $X_2$ have the aforesaid meanings, said reaction taking place in the presence of formaldehyde and an oxidation catalyst.

DETAILED DESCRIPTION OF THE INVENTION

The process of the present invention proceeds in accordance with the following scheme:

where, in formulas (I) and (II), $X_1$ and $X_2$ have the aforesaid meanings. Preferably $X_1$ and $X_2$ represent a linear or branched C1-C4 alkyl; when the —O-T-O— structure is present, T is preferably chosen from methylene, ethylene, propylene and 2,2-dimethylpropylene.

Particularly preferred are compounds in which $X_1$ is the same as $X_2$ and represents a C1-C2 alkyl, and those in which $OX_1$ and $OX_2$ together form a —O-T-O— group where T is methylene.

Typical alcohols of formula (II) are for example 3,4-dimethoxy benzyl alcohol, 3,4-diethoxy benzyl alcohol, 3,4-methylenedioxy benzyl alcohol (piperonyl alcohol) and 3-ethoxy-4-methoxy benzyl alcohol.

The oxidation can be efficiently conducted in the presence of common homogeneous or heterogeneous catalysts, the use of highly active specific catalysts not being required.

The term "homogeneous catalysts" means those soluble in the reaction environment, which typically consists of an inert organic solvent such as toluene; the term "heterogeneous catalysts" means those insoluble in said environment.

Preferred homogeneous catalysts include aluminium, titanium and zirconium alkoxides and aryloxides; aluminium isopropoxide, zirconium isopropoxide, aluminium t-butoxide, aluminium phenoxide; aluminium isopropoxide is particularly preferred.

Preferred heterogeneous catalysts include zirconiums, hydrotalcites or others such as titanium dioxide or alumina. Zirconiums used are commercial zirconiums such as XZO 632/03 from Melcat, ZHSA and HWA-ZHSA from Millenium. Hydrotalcites used are commercial hydrotalcites, such as Pural MG61, MG50, MG70 from Sasol, Sorbacid 696 and 911 from SudChemie, Hycite 713 from SudChemie.

The homogeneous catalysts (such as aluminium, titanium or zirconium alkoxides or aryloxides) are used in quantities varying between 5% and 50% molar, preferably between 5% and 30%, more preferably between 8% and 25%, even more preferably between 8% and 20%, relative to the moles of the compound of formula (II).

The heterogeneous catalysts are used in quantities between 5% and 80% w/w, preferably between 10 and 50% w/w, more preferably between 15 and 30% w/w relative to the compound of formula (II).

The reaction is conducted in a suitable inert solvent such as toluene, xylene, mesitylene, dioxane, chlorobenzene, tetrachloroethane, tetrachloroethylene; toluene and xylene are preferred; toluene is particularly preferred.

The reaction temperature is between 50° C. and 160° C., preferably between 80° C. and 120° C., more preferably between 90° C. and 110° C.

The formaldehyde is conveniently used in its commercial polymeric form paraformaldehyde, which is added in a molar ratio from 1 to 5 times the moles of the compound of formula (II) to be oxidized. A molar ratio from 1 to 3 times is preferred.

The present invention has extremely important industrial implications in that the 3,4-dioxo-substituted aldehydes (particularly piperonyl aldehyde or piperonal) can for example be used directly as fragrances or as intermediates for pharmaceutical products. The present process enables a rapid and convenient access path to the aforesaid products.

The use of formaldehyde as a hydrogen acceptor for the oxidation of the compounds of formula (II) has shown considerable advantages in carrying out the Oppenauer reaction to obtain the corresponding aromatic aldehyde, with high yields and almost quantitative conversions.

Some preparation examples are given below by way of non-limiting illustration.

EXPERIMENTAL PART

EXAMPLE 1

20.0 g (0.136 mols) of piperonyl alcohol, 200 g of toluene and 2.7 g (0.013 mols) of aluminium isopropoxide (homogeneous catalyst) are introduced into a 1000 ml flask. The solution is heated under reflux and 8.00 g (0.263 mols) of p-formaldehyde are slowly added. At the end of the addition the mixture is left for about 2 hours under reflux, after which it is cooled and 300 ml of an aqueous 1 M sodium hydroxide solution are added. The phases are separated and the organic solution evaporated under vacuum (at 30° C./21 mbar) to obtain a crude reaction product containing 3,4-methylenedioxybenzaldehyde with a GC yield of 99.3% and a conversion of 100%.

EXAMPLE 2

2.5 g of zirconium ($ZrO_2$)XZO 632/03 from Melcat (heterogeneous catalyst) and 100 g of toluene are introduced into a 500 ml flask. The mixture is heated under reflux to azeotropically eliminate the water present, then, after cooling, 10.0 g (0.066 mols) of piperonyl alcohol are added. After heating under reflux, 4.93 g (0.164 mols) of p-formaldehyde are slowly added.

At the end of the addition, the solution is maintained for about 4 hours under reflux, then cooled and the catalyst filtered off. The organic solution is evaporated under vacuum (at 30° C./21 mbar) to obtain a crude reaction product containing 3,4-methylenedioxybenzaldehyde with a 99% GC yield and a conversion of 100%.

EXAMPLE 3

Following the method described in example 2, 10.0 g (0.164 mols) of piperonyl alcohol in 100 g of toluene are reacted with 4.93 g (0.164 mols) of p-formaldehyde in the presence of 2.5 g Pural MG61 from Sasol (a hydrotalcite) (heterogeneous catalyst). After evaporating the organic solution under vacuum (at 30° C./21 mbar) a crude reaction product containing 3,4-methylenedioxybenzaldehyde is obtained with a 99.8% GC yield and a conversion of 100%.

EXAMPLE 4 (COMPARATIVE)

In this case the formaldehyde is replaced by benzaldehyde.
Operating as described in example 1, 15.2 g (0.1 mols) of piperonyl alcohol are reacted in 200 g of toluene with 31.2 g (0.3 mols) of benzaldehyde in the presence of 2.04 g (0.01 mols) of aluminium isopropoxide.

After cooling and adding 300 ml of an aqueous 1 M sodium hydroxide solution, the phases are separated and the organic solution evaporated under vacuum (at 30° C./21 mbar) to obtain a crude reaction product containing 3,4-methylenedioxybenzaldehyde with a 83% GC yield and a conversion of 95%.

EXAMPLE 5 (COMPARATIVE)

In this case the formaldehyde is replaced by cyclohexanone. Similarly to that described in example 4 and using the same quantities, the reaction is conducted with 19.6 g (0.2 mols) of cyclohexanone as hydrogen acceptor.

The crude reaction product contained 3,4-methylenedioxybenzaldehyde with a 58% GC yield and a conversion of 70%.

EXAMPLE 6 (COMPARATIVE)

Similarly to that described in example 4 and using the same quantities, the reaction is conducted with 22.8 g (0.2 mols) of 2,5-dimethylpentanone as hydrogen acceptor.

The crude reaction product contained 3,4-methylenedioxybenzaldehyde with a 13.7% GC yield and a conversion of 22%.

Examples 1-4, when compared with comparative examples 5 and 6, show that the use of formaldehyde as hydrogen acceptor has led to a dramatic increase in yield and conversion.

EXAMPLE 7 (COMPARATIVE)

Operating as described in example 1, 10.8 g (0.1 mols) of benzyl alcohol are reacted, in 100 g toluene, with 6.0 g (0.29 mols) of p-formaldehyde in the presence of 2.04 g (0.01 mols) of aluminium protoxide.

After cooling and adding 300 ml of an aqueous 1 M sodium hydroxide solution, the phases are separated and the organic solution evaporated under vacuum (at 25° C./21 mbar) to obtain a crude reaction product containing benzaldehyde with a 73.6% GC yield and a conversion of 83.1%.

EXAMPLE 8

Following the method described in example 2, 5.0 g (0.0003 mols) of piperonyl alcohol are reacted with 2.5 g (0.083 mols) of p-formaldehyde in 50.0 g of toluene in the presence of 1.25 g of Sorbacide 696 (a hydrotalcite produced by SudChemie, previously calcinated at 400° C.).

The mixture is maintained under reflux for 2 hours. The catalyst is cooled and filtered off. The organic solution is evaporated under vacuum (at 30° C./21 mbar) to obtain a crude reaction product containing 3,4-methylenedioxybenzaldehyde with a 92% GC yield and a conversion of 99.5%.

EXAMPLE 9

Operating as described in example 2, 5.0 g (0.03 mols) of veratric alcohol (3,4-dimethoxy benzyl alcohol) are reacted, in 50 g of toluene, with 2.25 g (0.075 mols) of p-formaldehyde in the presence of 1.25 g of zirconia ($ZrO_2$) XZO 632/03 from Melcat.

After filtering off the catalyst and evaporating under vacuum (at 30° C./21 mbar) a crude reaction product containing veratric aldehyde is obtained with a 96.5% GC yield and a conversion of 98.3%.

The examples presented herein demonstrate that the Oppenauer reaction, when carried out in the presence of formaldehyde on the 3,4-dioxo-substituted benzyl alcohols of formula (II), proceeds with an unexpectedly high efficiency. The efficiency is evident from both yield and conversion percentages.

By comparison, the reaction proceeds in a much less efficient manner (in terms of both yield and conversion) when undertaken with formaldehyde on benzyl alcohols different from those of formula (II), or when undertaken on the same benzyl alcohols of formula (II) but in the presence of hydrogen acceptors other than formaldehyde.

The invention claimed is:

1. Process for the synthesis of compounds of formula (I)

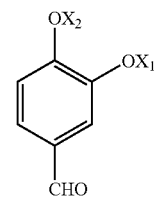

(I)

wherein $X_1$ and $X_2$, the same or different from one another, represent hydrogen, linear or branched C1-C8 alkyl, with the proviso that at least one of $X_1$ and $X_2$ is different from hydrogen, or ($OX_1$) and ($OX_2$), taken together, form a —O-T-O— group where T is a C1-C3 alkylene optionally substituted with C1-C5 alkyl, comprising treating a compound of formula (II)

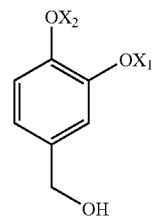

(II)

where $X_1$ and $X_2$ have the aforesaid meanings, with formaldehyde in the presence of an oxidation catalyst chosen from aluminium alkoxides, zirconiums, hydrotalcites, and zirconium alkoxides.

2. Process as claimed in claim 1, wherein $X_1$ and $X_2$ represent a linear or branched C1-C4 alkyl, or $X_1$ and $X_2$ together form the —O-T-O— structure, where T is chosen from methylene, ethylene, propylene and 2,2-dimethylpropylene.

3. Process as claimed in claim 1, wherein the compound of formula (II) is chosen from 3,4-dimethoxy benzyl alcohol, 3,4-diethoxy benzyl alcohol, 3,4-methylenedioxy benzyl alcohol, 3-ethoxy-4-methoxy benzyl alcohol.

4. Process as claimed in claim 1, wherein the aluminium alkoxide is used in a quantity between 5% and 50% molar relative to the moles of the compound of formula (II).

5. Process as claimed in claim 4 wherein the aluminium alkoxide is used in a quantity between 5% and 30% relative to the moles of the compound of formula (II).

6. Process as claimed in claim 5, wherein the aluminium alkoxide is used in a quantity between 8% and 25% relative to the moles of the compound of formula (II).

7. Process as claimed in claim 6, wherein the aluminium alkoxide is used in a quantity between 8% and 20% relative to the moles of the compound of formula (II).

8. Process as claimed in claim 1, wherein the hydrotalcite or zirconium is used in a quantity between 5% and 80% w/w, with respect to the weight of compound of formula (II).

9. Process as claimed in claim 8, wherein the hydrotalcite or zirconium is used in a quantity between 10 and 50% w/w, with respect to the weight of compound of formula (II).

10. Process as claimed in claim 9, wherein the hydrotalcite or zirconium is used in a quantity between 15 and 30% w/w, with respect to the weight of compound of formula (II).

11. Process as claimed in claim 1, conducted at a temperature between 50° C. and 160° C.

12. Process as claimed in claim 1, conducted at a temperature between 80° C. and 120° C.

13. Process as claimed in claim 1, conducted at a temperature between 90° C. and 110° C.

14. Process as claimed in claim 1, wherein the formaldehyde is present in a molar ratio of between 1 and 5 relative to the compound of formula (II).

15. Process as claimed in claim 14, wherein the formaldehyde is present in a molar ratio of between 1 and 3 to the compound of formula (II).

* * * * *